(12) United States Patent
Bernick et al.

(10) Patent No.: US 9,890,417 B2
(45) Date of Patent: Feb. 13, 2018

(54) SIGNAL AMPLIFICATION OF FLUORESCENCE IN SITU HYBRIDIZATION

(71) Applicant: Agilent Technologies, Inc., Loveland, CO (US)

(72) Inventors: Kristin Bernick, San Jose, CA (US); Robert Ach, San Francisco, CA (US); Mistuni Ghosh, Santa Clara, CA (US); Brian Smart, San Jose, CA (US)

(73) Assignee: Agilent Technologies, Inc., Loveland, CO (US)

( * ) Notice: Subject to any disclaimer, the term of this patent is extended or adjusted under 35 U.S.C. 154(b) by 7 days.

(21) Appl. No.: 14/531,563

(22) Filed: Nov. 3, 2014

(65) Prior Publication Data
US 2016/0122800 A1 May 5, 2016

(51) Int. Cl.
*C12Q 1/68* (2006.01)

(52) U.S. Cl.
CPC .................................. *C12Q 1/682* (2013.01)

(58) Field of Classification Search
None
See application file for complete search history.

(56) References Cited

U.S. PATENT DOCUMENTS

| 8,435,735 | B2 | 5/2013 | Lohse | |
|---|---|---|---|---|
| 8,551,697 | B1 | 10/2013 | Bashkirov et al. | |
| 2005/0181394 | A1* | 8/2005 | Steemers | B82Y 30/00 435/6.11 |
| 2007/0134682 | A1* | 6/2007 | Holliger | C12N 15/1075 435/6.14 |
| 2008/0138801 | A1 | 6/2008 | He | |
| 2014/0228239 | A1 | 8/2014 | McCoy et al. | |

FOREIGN PATENT DOCUMENTS

| EP | 2398908 | 8/2013 |
|---|---|---|
| EP | 2398907 | 4/2014 |
| WO | WO2009036760 | 3/2009 |
| WO | WO2010048366 | 4/2010 |
| WO | WO2012143010 | 10/2012 |

OTHER PUBLICATIONS

Lohse, et al. "Improved Catalyzed Reporter Deposition, iCARD", Bioconjugate Chem., 2014, 25, 1036-1042.
Lohse, et al. "Counting single molecules in tissue by improved catalyzed reporter deposition (iCARD)", Chemical synthesis, Immunohistochemistry staining protocols, Chemical structure of reporter, 5 pages, 2014.
Li, et al. "A new class of homogeneous nucleic acid probes based on specific displacement hybridization" Nucleic Acids Researcil, 2002, vol. 30, No. 2 e5.
Notification of Transmittal of the International Search Report and the Written Opinion of the International Searching Authority, or the Declaration for PCT/US2015/058608, dated Feb. 19, 2016, 15 pages.

* cited by examiner

*Primary Examiner* — James Martinell

(57) ABSTRACT

Among other things, this disclosure provides a method of detecting a target nucleic acid. Aspects of the method include: (a) obtaining a labeled nucleic acid probe that is complementary to a target nucleic acid, wherein the probe comprises a capture tag; (b) hybridizing the probe with the target nucleic in a fixed cell, in situ, to produce a duplex; (c) linking the probe in the duplex to a peroxidase conjugate via the capture tag to produce a peroxidase-labeled duplex; and (d) incubating the peroxidase-labeled duplex with a peroxidase substrate, wherein the peroxidase activity of the peroxidase conjugate catalyzes deposition of the substrate in the vicinity of the duplex, thereby producing a detectable signal.

20 Claims, 4 Drawing Sheets

FISH on Slide Grown Fibroblasts (SureFISH Hyb)

Bacteria FISH in FFPE (IQ Hyb)

SIGNAL AMPLIFICATION OF FLUORESCENCE IN SITU HYBRIDIZATION

BACKGROUND

Fluorescence in situ hybridization (FISH) is a powerful technology wherein nucleic acids are targeted by fluorescently labeled probes and then visualized via microscopy. FISH is a single-cell assay, making it especially powerful for the detection of rare events that might be otherwise lost in mixed or asynchronous populations of cells. In addition, because FISH is applied to fixed cell or tissue samples, it can reveal the positioning of chromosomes relative to nuclear, cytoplasmic, and even tissue structures, especially when applied in conjunction with immunofluorescent targeting of cellular components. FISH can also be used to visualize RNA, making it possible for researchers to simultaneously assess gene expression, chromosome position, and protein localization.

Signal amplification is of interest for fluorescence in situ hybridization (FISH) to provide visualization of smaller regions of nucleic acids, improve signal to noise/counteract situations of high background, overcome limitations of dim fluorophores, and improve performance for visualizing samples through microscope eye pieces instead of being aided by increased sensitivity of a camera. As such, methods for signal amplification that work for both RNA and DNA FISH are desirable.

SUMMARY

Among other things, this disclosure provides a method of detecting a target nucleic acid. Aspects of the method include: (a) obtaining a labeled nucleic acid probe that is complementary to a target nucleic acid, wherein the probe comprises a capture tag; (b) hybridizing the probe with the target nucleic acid in a fixed cell, in situ, to produce a duplex; (c) linking the probe in the duplex to a peroxidase conjugate via the capture tag to produce a peroxidase-labeled duplex; and (d) incubating the peroxidase-labeled duplex with a peroxidase substrate, wherein the peroxidase activity of the peroxidase conjugate catalyzes deposition of the substrate in the vicinity of the duplex, thereby producing a detectable signal.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
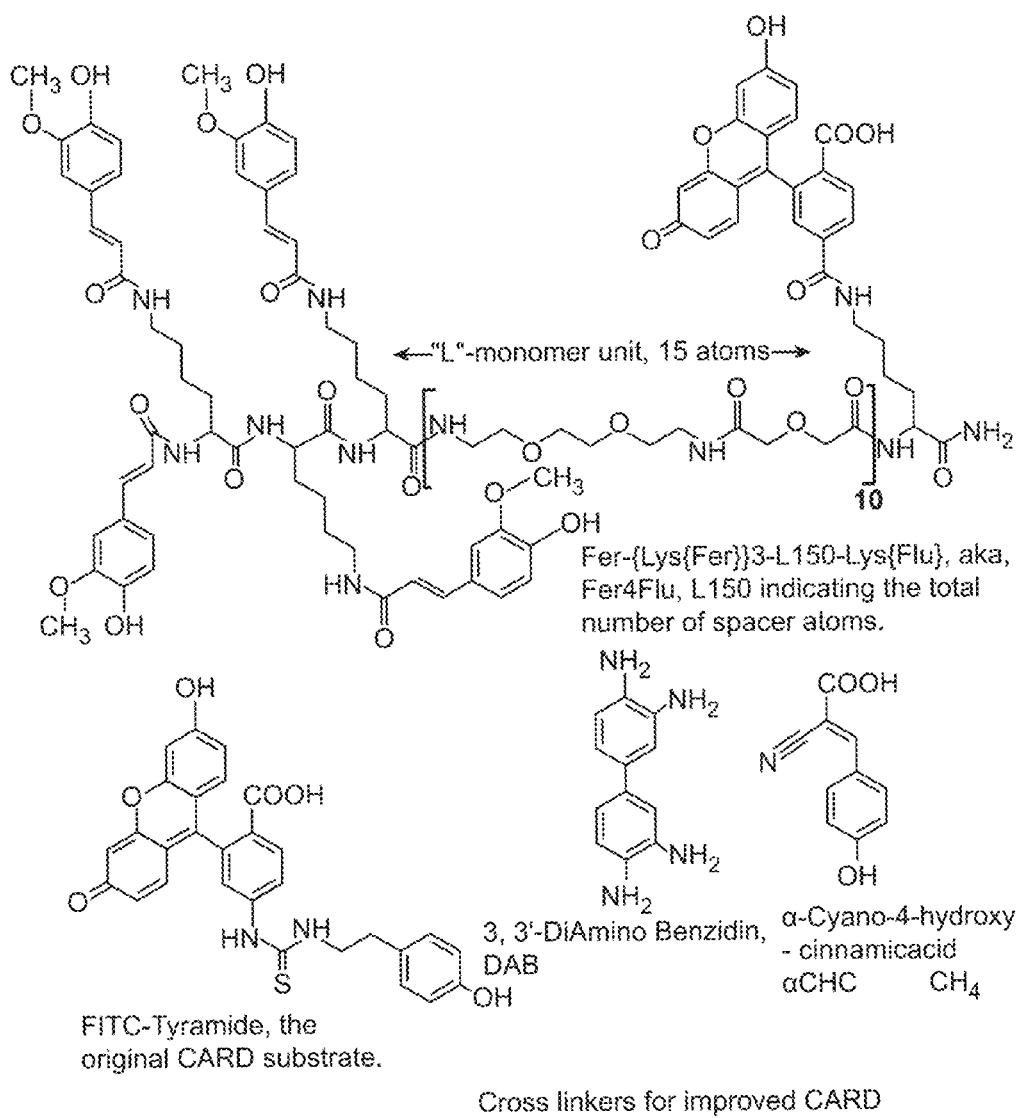
FIG. 1 shows the structures of exemplary compounds (Fer-4-Flu and αCHC) that can be used in the signal amplification method.
Figure 2:
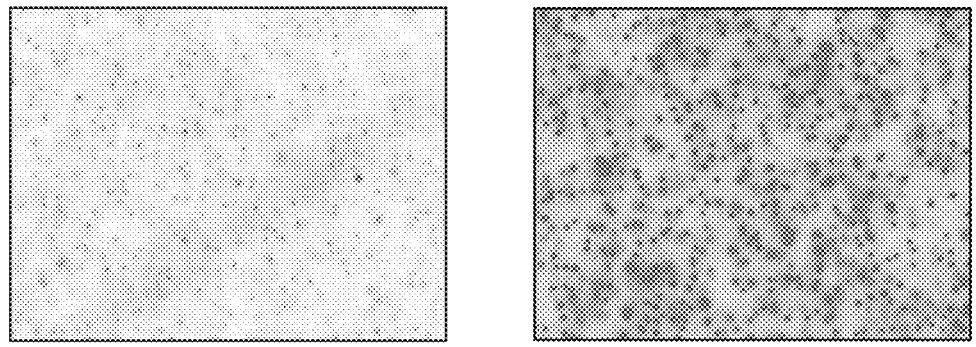
FIG. 2 shows signal amplification of DNA Fluorescence in Situ Hybridization (FISH) of EGFR gene using 2 hour IQ hybridization. Signal is clearly visible with 10 ms exposure (left) and significantly amplified with 100 ms exposure (right). Probes were not visible without amplification.
Figure 3:
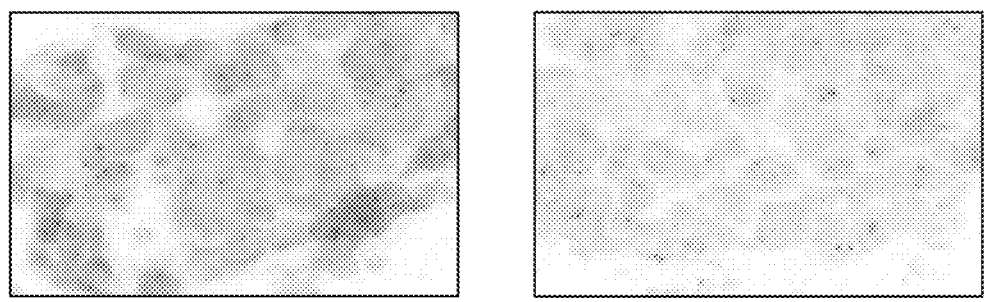
FIG. 3 shows signal amplification of two FISH probe sets (~50 kb in coverage) previously found to give lower than optimal signal without the aid of amplification. After amplification, signals are clearly visible through microscope eye pieces. 2 hour IQ hybridization is used.
Figure 4:
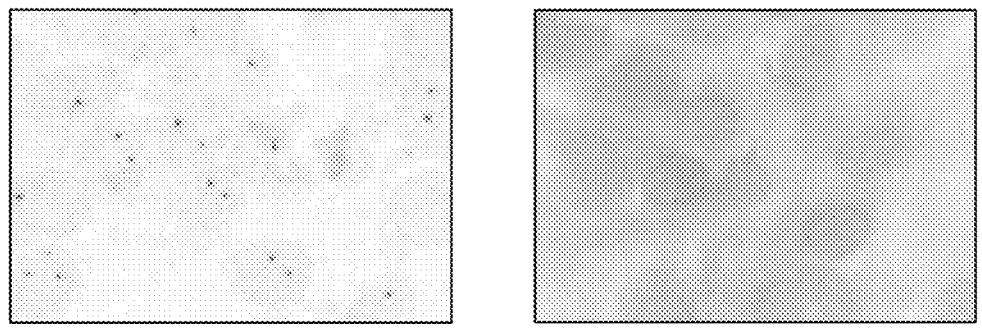
FIG. 4 shows signal amplification after overnight Sure-FISH hybridization on slide grown fibroblasts. Amplification provided 50 ms (left) exposure compared to 2.4 s exposure without amplification (right).
Figure 5:
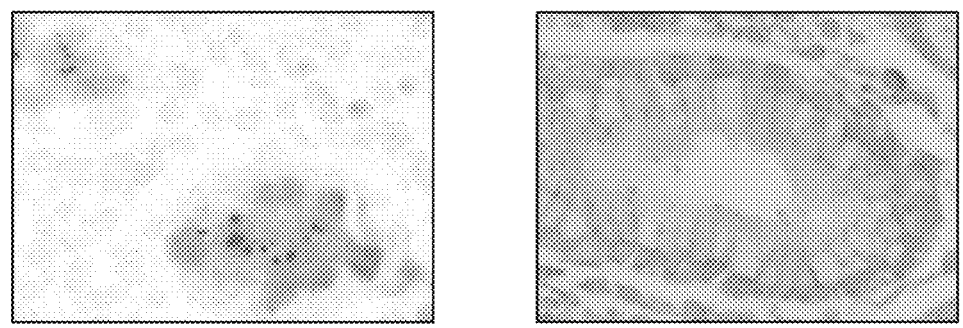
FIG. 5 shows that signal amplification provided visualization of H. pylori in FFPE stomach tissue section using 2 hour IQ hybridization (left). No visualization was possible without amplification (right).

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still may base pair to the non-target sequence due to complementarity of certain stretches of nucleotide sequence to the non-target sequence, percent complementarily may be calculated to assess the possibility of a non-specific (off-target) binding. In general, a complementary of 50% or less does not lead to non-specific binding. In addition, a complementary of 70% or less may not lead to non-specific binding under stringent hybridization conditions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of about 50 to 200 nucleotides and up to 300 nucleotides in length, or sometimes longer, e.g., up to 500 nt in length. Oligonucleotides may be synthetic and, in certain embodiments, are less than 300 nucleotides in length.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include poly-deoxyribonucleotides (DNA), poly-ribonucleotides (RNA), other nucleic acids that are C-glycosides of a purine or pyrimidine base, polypeptides (proteins), polysaccharides (starches, or polysugars), and other chemical entities that contain repeating units of like chemical structure.

The terms "plurality", "set" or "population" are used interchangeably to mean at least 2, at least 10, at least 100, at least 500, at least 1000, at least 10,000, at least 100,000, at least 1000,000, at least 10,000,000, at least 100,000,000, or more.

The term "in situ hybridization conditions" as used herein refers to conditions that allow hybridization of a nucleic acid to a complementary nucleic acid, e.g., a sequence of nucleotides in a RNA or DNA molecule and a complementary oligonucleotide, in a cell. Suitable in situ hybridization conditions may include both hybridization conditions and optional wash conditions, which conditions include temperature, concentration of denaturing reagents, salts, incubation time, etc. Such conditions are known in the art.

The term "duplex," or "duplexed," as used herein, describes two complementary polynucleotides that are base-paired, i.e., hybridized together.

The term "free in solution," as used here, describes a molecule, such as a polynucleotide, that is not bound or tethered to another molecule.

As used herein, the term "labeling" refers to attaching a detectable moiety to specific sites in a sample (e.g., sites containing an epitope for the antibody being used) such that the presence and/or abundance of the sites can be determined by evaluating the presence and/or abundance of the label.

As used herein, the term "fixed cell, in situ," refers to a cell that is fixed in place. In general terms, fixation of a cell of interest aims to terminate ongoing bioactivity of the cell and to preserve certain characteristics of the cells, such as the shape of the cell, the locations of components within the cell, and the identity of cell components. Any convenient method may be utilized to produce a fixed cell. Methods of interest include, but are not limited to, heat fixation, chemical fixation, e.g., using a chemical reagent to form covalent bonds to components of the cell, thereby immobilizing the components, or using a chemical agent to terminate the activity of the cell. Chemical fixation may be performed using agents such as formaldehyde, ethanol, methanol or picric acid.

The fixed cell may be comprised in a cell sample or a tissue sample. Examples of suitable samples are tissue sections, tissue blocks, a gel layer, a cell, a cell layer, a tissue array, yeasts or bacteria on a culture plate, membrane, paper or fabric, or a carrier with spots of isolated or synthetic nucleic acid molecules. In general the sample may comprise a carrier made of glass, plastic, paper, a membrane (e.g. nitrocellulose) or fabric. For example a tissue section is usually applied on a glass slide or coverslip. A cell layer could also be provided on a glass slide or on a plastic dish. Unicellular organisms may be provided on culture plates, on filter paper or on a fabric.

As used herein, the term "planar sample" refers to a substantially planar, i.e., two dimensional, material that contains cells. A planar sample can be made by, e.g., growing cells on a planar surface, depositing cells on a planar surface, e.g., by centrifugation, or by cutting a three dimensional object that contains cells into sections and mounting the sections onto a planar surface. The cells may be fixed using any number of reagents including formalin, methanol, paraformaldehyde, methanol:acetic acid and other reagents listed above or below.

As used herein, the term "tissue section" refers to a piece of tissue that has been obtained from a subject, fixed, sectioned, and mounted on a planar surface, e.g., a microscope slide.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a planar surface, e.g., a microscope slide.

As used herein, the term "resin embedded tissue section" refers to a piece of tissue, e.g. a biopsy that has been obtained from a subject, fixed, (e.g., in 3-5% glutaraldehyde in 0.1M phosphate buffer), dehydrated, infiltrated with epoxy or methacrylate resin, cured, cut into thin sections, and then mounted on a planar surface, e.g., a microscope slide.

As used herein, the term "cryosection" refers to a piece of tissue, e.g. a biopsy that has been obtained from a subject, snap frozen, embedded in optimal cutting temperature embedding material, frozen, cut into thin sections and fixed (e.g. in methanol or paraformaldehyde) and mounted on a planar surface, e.g., a microscope slide.

As used herein, the term "linking" refers to non-covalent and covalent linking of two moieties of interest. Covalent linking may involve the chemical reaction of two compatible functional groups (e.g., two chemoselective functional groups, an electrophile and a nucleophile, etc.) to form a covalent bond between the two moieties of interest. Non-covalent linking may involve specific binding between two moieties of interest (e.g., two affinity moieties such as a hapten and an antibody or a biotin moiety and a streptavidin, etc).

A "linkage" may be non-covalent or covalent. As used herein, the term "cleavably linked to" or "cleavable linkage" refers to a linkage that is selectively breakable using a stimulus (e.g., a physical, chemical or enzymatic stimulus) that leaves the moieties to which the linkages joins intact.

As used herein, the term "linker" or "linkage" refers to a linking moiety that connects two groups and has a backbone of 20 atoms or less in length. A linker or linkage may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the term "peroxidase conjugate" refers to a peroxidase enzyme of interest conjugated to a moiety that provides for linking of the peroxidase conjugate to an analyte or probe of interest (i.e., a linking moiety). In many cases, the peroxidase enzyme is covalently conjugated to the linking moiety. As such, the peroxidase conjugate may include a linking moiety that provides for covalent or non-covalent linking (e.g., as described herein, such as a partner of a chemoselective tag or a partner of an affinity tag) to the analyte or probe of interest. Peroxidase conjugates of interest include, but are not limited to, a peroxidase enzyme, such as horse radish peroxidase (HRP) or soybean peroxidase (SP), covalently conjugated to a partner of a chemoselective tag (e.g., an azide or a cyclooctyne) or a partner of an affinity tag (e.g., an anti-fluorescein antibody or a streptavidin).

As used herein, the term "peroxidase substrate" refers to compound that includes a group capable of being acted upon by a peroxidase enzyme of interest. In general, peroxidase enzymes act upon phenol-containing groups using $H_2O_2$ as an oxidizing agent to produce phenoxyl radical intermediates and provide for oxidative coupling reactions with e.g., any convenient aromatic groups that are in the vicinity (e.g., as described by Henriksen et al. "The Structures of the Horseradish Peroxidase C-Ferulic Acid Complex and the Ternary Complex with Cyanide Suggest How Peroxidases Oxidize Small Phenolic Substrates" J. Biol. Chem. 1999, 274 (49), 35005-35011).

As used herein, the term "phenol-containing group" refers to a small organic group that is capable of forming a phenoxyl radical (i.e., an optionally substituted phenol). A variety of phenol-containing groups may be utilized in the peroxidase substrates. In some cases, the phenol-containing group that finds use in the peroxidase substrates may be a derivative of a 4-hydroxy-phenyl-alkyl-carboxylic acids (e.g., (3-(4-hydroxy-3-methoxyphenyl)-2-propenoic acid) or a derivative of a 4-hydroxy-phenyl-(substituted alkyl). Phenol containing groups of interest include, but are not limited to, a ferulic acid, a cinnamic acid, a cinnapinic acid, and derivatives thereof. The peroxidase substrate may include one or more phenol-containing groups, such as two or more, three or more, four or more, five or more, six or more, seven or more, eight or more, nine or more, or ten or more phenol-containing groups (e.g., phenol-containing groups in a dendrimer). The peroxidase substrate may further include a moiety that is not capable of being acted upon by the peroxidase enzyme, but which provides for detection of the substrate (e.g., a detectable moiety such as a fluorophore). As such, peroxidase substrate may include one or more phenol-containing groups (e.g., a ferulic acid, a cinnamic acid, a cinnapinic acid, or a derivative thereof) linked to a detectable moiety (e.g., a fluorophore or a biotin).

As used herein, the term "capture tag" refers to a moiety that is capable of: a) specifically binding to binding partner for the capture tag non-covalently (i.e., is an "affinity tag"); or b) selectively reacting with another chemoselective group to form a covalent bond (i.e., is a "chemoselective tag"). Examples of pairs of suitable affinity tags/binding pairs are numerous and include, but are not limited to: biotin/streptavidin, biotin/avidin, digoxigenin/anti-digoxigenin antibody, and fluorescein/anti-fluorescein antibody, although many others are known.

As used herein, the term "affinity tag" refers to a moiety that can be used to separate a molecule to which the affinity tag is attached from other molecules that do not contain the affinity tag. In certain cases, an "affinity tag" may specifically bind to a binding partner for the affinity tag, thereby facilitating the separation of the molecule to which the affinity tag is attached from other molecules that do not contain the affinity tag. Examples of affinity tags include, but are not limited to, a biotin moiety, digoxygenin, fluorescein, peptide tags and protein tags (e.g., his-tags and the like).

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

As used herein, the terms "chemoselective functional group" and "chemoselective group" are used interchangeably and refer to chemoselective reactive groups that selectively react with one another to form a covalent bond. Chemoselective functional groups of interest include, but are not limited to, thiols and maleimide or iodoacetamide, as well as groups that can react with one another via Click chemistry, e.g., azide and alkyne groups (e.g., cyclooctyne groups).

As used herein, the term "crosslinker" or "crosslinker capable of peroxidase-catalyzed radical chain polymerization" refers to a peroxidase substrate (e.g., as described herein) that is capable of being acted upon by a peroxidase enzyme of interest to produce a phenoxyl radical initiator of radical chain polymerization (see, e.g., Hollmann et al., "Enzyme Initiated Radical Polymerizations", Polymers 201, 4, 759-793). Crosslinker may form a polymer comprised of crosslinker-derived monomers and/or any convenient aromatic molecules capable of reaction with the phenoxyl radical intermediate (e.g., a fluorescent compound that is a peroxidase substrate). Any convenient crosslinkers may be utilized in the subject methods. Crosslinkers of interest include, but are not limited to, 3,3'-diamino benzidin (DAB) and alpha-cyano-4-hydroxy-cinnamic acid (α-CHC).

As used herein, the term "insoluble adduct" refers to an adduct product of the action of a peroxidase enzyme upon a peroxidase substrate, where the adduct is insoluble because it is a precipitate or is immobilized on a support. In general, the "insoluble adduct" refers to the peroxidase-catalyzed product of a precipitating peroxidase substrate, e.g., a substrate such as 3,3'-diamino benzidin (DAB) or alpha-cyano-4-hydroxy-cinnamic acid (α-CHC).

As used herein, the term "hapten" refers to a small molecule antigen that specifically binds to an anti-hapten antibody. Haptens of interest include, but are not limited to, a biotin moiety, a fluorophore, digoxygenin, and the like.

As used herein, the term "HRP polymer" refers to a polymer linked to two or more peroxidase enzymes (e.g., HRP). A variety of HRP polymers that include multiple peroxidase enzymes are available and may be utilized in the method.

As used herein, the term "HRP-azide conjugate" refers to a peroxidase enzyme linked to one or more azido chemoselective functional group.

As used herein, the term "HRP-cyclooctyne conjugate" refers to a peroxidase enzyme linked to one or more cyclooctyne chemoselective functional group.

Other definitions of terms may appear throughout the specification.

DETAILED DESCRIPTION

In order to further illustrate the present invention, the following specific examples are given with the understanding that they are being offered to illustrate the present invention and should not be construed in any way as limiting its scope.

Figure 6:
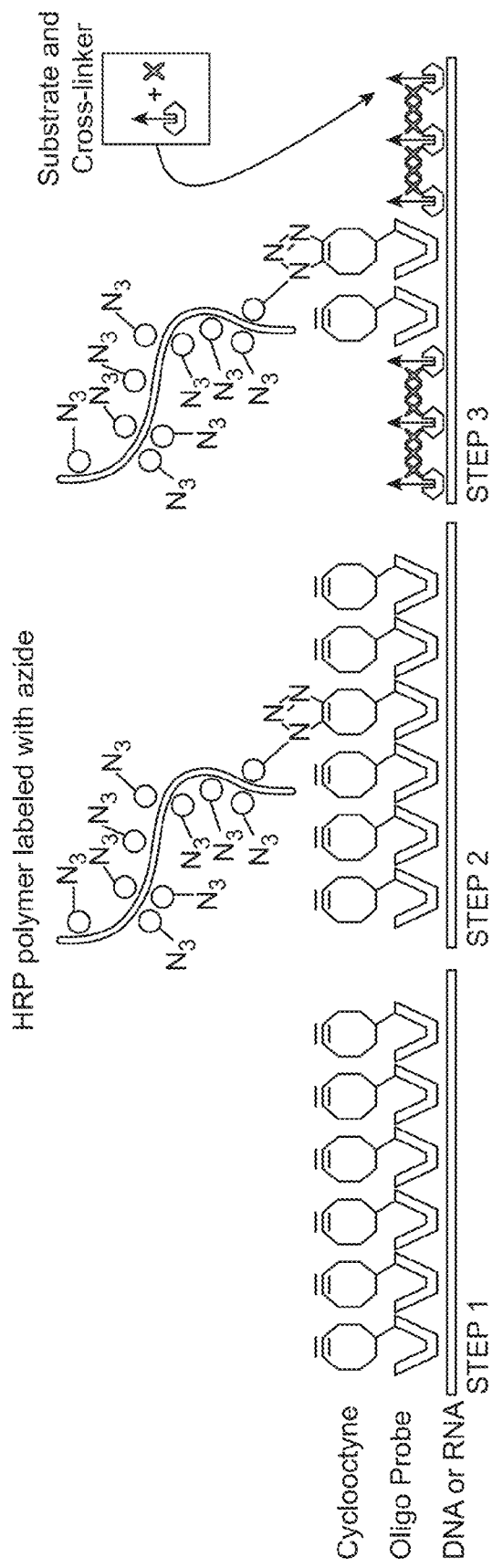
FIG. 6 shows an example of cyclooctyne labeled oligo probes, reaction with HRP polymer labeled with azide, and HRP-catalyzed reaction and crosslinking with Fer4-Flu for RNA or DNA FISH.

In certain embodiments, the method comprises obtaining a labeled nucleic acid probe that is complementary to a target nucleic acid and comprises a capture tag. The probe may be of any length, e.g., in the range of 50-200 nucleotides in length, and one or more capture tags may be located at any convenient position along the probe, at or proximal to the 5' end, at or proximal to the 3' end, at a central location of the probe, or along the probe. In some embodiments, the probe may be made to contain the capture tag and in other embodiments the capture tag may be conjugated to the probe after it is made. As will be discussed in greater detail below, the capture tag used should be capable of specifically linking the nucleic acid of the probe to a peroxidase conjugate. In some cases, the capture tag may be an affinity tag, in which case it binds to its partner non-covalently. In these embodiments, the probe may contain a biotin moiety or a hapten, which bind to streptavidin and antibodies, respectively). In other cases, the capture tag may contain a chemoselective group, in which case it binds to its partner covalently, e.g., via Click chemistry or another suitable reaction. For example, a cyclooctyne could be incorporated into all oligonucleotide probes during PCR (which would have the added benefit of using hydrophobicity of the cyclooctyne as a way to purify only the desired strand of the double stranded PCR product) and the HRP/polymer conjugate could easily be labeled on lysine residues using an azide-NHS molecule, such as the NHS ester of azidoacetic acid (FIG. 6). Furthermore, there are many other bioorthogonal chemistries that could be used for multiplexing, such as alkoxyamine/aldehyde chemistry (Lang et al, ACS Chem. Biol. 2014, 9, pp. 16-20).

In certain embodiments, the probes used in the method may be designed and/or made using methods set forth in US20040101846, U.S. Pat. No. 6,251,588, US20060115822, US20070100563, US20080027655, US20050282174, patent application Ser. No. 11/729,505, filed March 2007 and patent application Ser. No. 11/888, 059, filed Jul. 30, 2007 and references cited therein, for example. In certain embodiments, the oligonucleotides precursors for the probes may be synthesized in an array using in situ synthesis methods in which nucleotide monomers are sequentially added to a growing nucleotide chain that is attached to a solid support in the form of an array. Such in situ fabrication methods include those described in U.S. Pat. Nos. 5,449,754 and 6,180,351 as well as published PCT application no. WO 98/41531, the references cited therein, and in a variety of other publications. In one embodiment, the oligonucleotide composition may be made by fabricating an array of the oligonucleotides using in situ synthesis methods, and cleaving oligonucleotides from the array. Subsets of the oligonucleotides may be amplified by PCR prior to use (e.g., by using PCR using primer sites that are at the terminal regions of the oligonucleotides) and the ends of the PCR products may be removed by digestion by a Type IIs restriction enzyme. In some embodiments, if PCR products are used to generate the probes, then one of the strands of the PCR products may be removed prior to use, thereby producing a single-stranded probe. In many embodiments, however, the probe used may contain both strands of the PCR products (although in denatured form).

In one exemplary embodiment, FISH probes can be labeled with biotin using the Universal Linkage System (ULS™, KREATECH Diagnostics; van Gijlswijk et al Universal Linkage System: versatile nucleic acid labeling technique Expert Rev. Mol. Diagn. 2001 1:81-91). In brief, ULS™ is based on the stable binding properties of platinum (II) to nucleic acids. The ULS molecule consists of a monofunctional platinum complex coupled to a detectable molecule of choice. Alternative methods may be used for labeling the probes, for example, as set out in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.).

In the next step, the probes are hybridized with the target nucleic acids in a fixed cell, in situ, to result in one or more duplexes. In this step, the probes are hybridized to nucleic acid (e.g., DNA or RNA) that is in the interior of a fixed cell. As noted above, such a cell is usually mounted on the surface of a planar support, e.g., a glass microscope slide, and can be made by, e.g., growing cells on a planar surface and then fixing them in place, depositing cells on a planar surface, e.g., by centrifugation, and then fixing them, or by cutting a three dimensional object that contains fixed cells (e.g., FFPE tissue) into sections and mounting the sections onto a planar surface. The cells may be fixed using any number of reagents including formalin, methanol, paraformaldehyde, methanol:acetic acid and other reagents listed above or below.

In certain embodiments, cells can be harvested from a biological or non-biological sample using a standard technique. For example, cells can be harvested by centrifuging a sample and resuspending the pelleted cells in, for example, phosphate-buffered saline (PBS). After re-centrifuging the cell suspension to obtain a cell pellet, the cells can be fixed in a solution such as an acid alcohol solution, an acid acetone solution, or an aldehyde such as formaldehyde, paraformaldehyde, or glutaraldehyde. For example, a fixative containing methanol and glacial acetic acid in a 3:1 ratio, respectively, can be used as a fixative. A neutral buffered formalin solution also can be used (e.g., a solution containing approximately 1% to 10% of 37-40% formaldehyde in an aqueous solution of sodium phosphate). Slides containing the cells can be prepared by removing a majority of the fixative, leaving the concentrated cells suspended in only a portion of the solution. Methods for fixing cells are known in the art and can be adapted to suit different types of cells, if needed. Determination of suitable fixation/permeabilization protocols are carried out routinely in the art. Other techniques that involve, e.g., sectioning tissue sections, are well known.

In this step, the cells are treated to fix the target nucleic acid molecules (e.g., transcripts) in place and to increase access of the probes. The probe may be either a labeled DNA probe or an RNA probe that is complementary to the target sequence. The probe hybridizes to the target sequence at elevated temperature, and then the excess probe is washed away (after prior hydrolysis using RNase in the case of unhybridized, excess RNA probe, if necessary). In these embodiments, the cells are contacted with the labeled probes under in situ hybridizing conditions, where "in situ hybridizing conditions" are conditions that facilitate annealing between a nucleic acid and the complementary nucleic acid. Hybridization conditions vary, depending on the concentrations, base compositions, complexities, and lengths of the probes, as well as salt concentrations, temperatures, and length of incubation. For example, some in situ hybridizations may be performed in hybridization buffer containing 1-2 times SSC, 50% formamide, and blocking DNA to suppress non-specific hybridization. In general, hybridization conditions include temperatures of about 25° C. to about 55° C., and incubation times of about 0.5 hours to about 96 hours. Suitable hybridization conditions for a certain probe and target can be determined via experimentation which is routine for one of skill in the art.

Solution parameters such as temperature, salt and/or detergent concentration can be changed to alter the stringency of the hybridization. In certain embodiments, the method generally comprises fixing a sample, hybridizing the probe to RNA or DNA molecules contained within the cells of the fixed sample, and washing the hybridized sample to remove non-specific binding. In situ hybridization assays and methods for sample preparation are well known to those of skill in the art and need not be described in detail here. Fluorescence in situ hybridization methods have been extensively reviewed (see, e.g., O'Conner, Nature Education 2008 1:171 and Jin et al, J. Clinical Laboratory Analysis 1997 11: 2-9) the conditions for performing this step of the method may be adapted from known methods (see, e.g., Yamada et al, Cytogenet. Genome Res. 2011 132: 248-54, Rogan et al, Genome Res. 2001 11:1086-94, Kwon, BMB Rep. 2013 46:65-72 and Tanke et al, Histochem J. 1995 27:4-14). Details of how FISH can be performed on microbial samples can be found in, for example, Amann R. et al., 1995, Microbiol. Rev. 59(1): 143-69; Bruns and Berthe-Corti, 1998, Microbiology 144, 2783-2790; Vesey G. et al., 1998, J. App. Microbiol. 85, 429-440; and Wallner G. et al., 1995, Appl. Environ. Microbiol. 61(5): 1859-1866, and US20100081131, which are incorporated by reference herein.

The resulting duplex is detected by linking the probe in the duplex to a peroxidase conjugate and then incubating the peroxidase-labeled duplex with a detectable (e.g., fluorescently labeled) peroxidase substrate, wherein the peroxidase activity of the peroxidase conjugate catalyzes deposition of a fluorophore in the vicinity of the duplex. This linking step may be non-covalent or covalent. For example, in some embodiments, the capture tag may be a fluorophore (e.g., fluorescein or a cyanine dye) and the peroxidase conjugate may comprise an anti-fluorophore antibody. In other embodiments, the capture tag may be a biotin moiety, and the peroxidase conjugate may comprise streptavidin. In alternative embodiments, the capture tag may comprises a chemoselective group selected from the group consisting of an alkyne, a cyclooctyne, an azide, a phosphine, a maleimide, a thiol, an alkoxyamine and an aldehyde, for example, where the peroxidase conjugate contains a group that reacts with the chemoselective group to produce a covalent bond. For example, the peroxidase may contain an azide or cyclooctyne and the linking may be done via Click chemistry.

The peroxidase used in the method may be any suitable peroxidase. Horseradish peroxidase may be used in some cases, although any peroxidase having a similar activity may be used (i.e., enzymes having an activity defined as EC 1.11.1.7, using IUBMB nomenclature).

The peroxidase substrate used in the method may be any convenient peroxidase substrate (e.g., as described herein). In general terms, an immobilized peroxidase acts upon a peroxidase substrate using $H_2O_2$ as an oxidizing agent to produce reactive phenoxyl radical intermediates which can covalently link with e.g., any convenient aromatic groups that are in the vicinity. In some cases, the reactive phenoxyl intermediates covalently link to one or more moieties such as a protein residue sidechain such as a tyrosine.

As such, by the action of the immobilized peroxidase upon multiple copies of the peroxidase substrate, multiple peroxidase-modified substrate molecules are immobilized in the vicinity of the peroxidase providing for high density labelling of that location. When the peroxidase substrate includes a detectable label such as a chromophore or a fluorophore, the action of the peroxidase may provide for signal amplification, e.g., increases in detection sensitivity of 100-fold or more as compared to a non-amplified signal. In some case, the signal amplification described herein may be referred to as Catalyzed Reporter Deposition (CARD), see e.g., the methods and reagents described by Bobrow et al., J. Immunol. Methods. 1989 Dec. 20; 125(1-2):279-85. Any convenient CARD reagents and substrates may be utilized in the method.

In some instances, the peroxidase substrate may include one or more phenol-containing groups (e.g., a ferulic acid, a cinnamic acid, a cinnapinic acid, or a derivative thereof) linked to a detectable moiety (e.g., a fluorophore or a biotin). As such, in some cases, the peroxidase substrate includes a fluorescent moiety that provides for detection of the substrate via fluorescence. Any convenient fluorophore may find use in the peroxidase substrate. The peroxidase activity of the peroxidase conjugate catalyzes deposition of a fluorophore in the vicinity of the duplex.

In certain embodiments of the method, the peroxidase substrate used may be a fluorescent compound described by the formula (I): $(R^1)_n$—$(X)_q$—$(R^2)_m$ (I), wherein each $R^1$ is independently, a phenol-containing group (e.g., a ferulic acid, a cinnamic acid or a cinnapinic acid group); each $R^2$ is a fluorophore-containing group; each X is a linker group or a chemical bond; and m, n and q are each independently an integer from 1 to 15 (e.g., 1 to 10).

In some instances, n is 1, 2, 3, 4, 5 or 6. In certain instances, n is 4. In some embodiments, q is 4, 5, 6, 7, 8, 9, 10, 11, 12, 13, 14 or 15. In certain embodiments, q is 10. In some cases, m is 1 or 2. In certain cases, m is 1. In certain embodiments of formula (I), the peroxidase substrate has a formula $(R^1)_4$—$(X)_{10}$—$R^2$.

In some embodiments, $R^1$ includes a ferulic acid, a cinnamic acid or a cinnapinic acid group, optionally linked to each other via any convenient linker. In some cases, $(R^1)_n$ includes n phenol containing groups selected from a ferulic acid, a cinnamic acid and a cinnapinic acid that are linked via amide bonds to a linker including n amino groups (e.g., a peptidic linker such as H-Lys$_{(n-1)}$-). In certain embodiments, $(R^1)_n$ is described by the formula Fer-Lys(Fer)$_{(n-1)}$-, where Fer is ferulic acid. In certain cases, n is 3, 4, 5 or 6.

The linker group X and integer q may be selected so as to provide for a linking group having a length sufficient to separate the fluorophore-containing group $R^2$ from the $R^1$ groups and minimize aggregation and/or quenching of the fluorophore. In some cases, the linker group X and integer q are selected so as to provide a linking backbone of 100 atoms or more between $R^1$ and $R^2$, such as a linking backbone of 110 atoms or more, 120 atoms or more, 130 atoms or more, 140 atoms or more, 150 atoms or more, 160 atoms or more, 180 atoms or more, 200 atoms or more, or even more.

In some embodiments, X is described by the formula: —NH—$(CH_2)_2$—$(OCH_2CH_2)_p$—$NHCO(CH_2)_rO(CH_2)_s$ CO— where p is 0, 1, 2, 3, 4 or 5, and r and s are independently 1, 2 or 3. In certain cases, p is 2, r is 1 and s is 1.

In certain embodiments, $R^2$ is a fluorophore directly linked to the linker group X. In some embodiments, $R^2$ includes an amino acid residue covalently linked to a fluorophore. Any convenient amino acid residues may be utilized. For example, $R^2$ may include a lysine residue where the sidechain amino group is covalently linked (e.g., via an amide bond) to a fluorophore (e.g., -Lys(fluorophore)-$NH_2$). Any convenient fluorophore may find use in the fluorophore-containing group $R^2$ of the peroxidase substrate. Fluorophores of interest, include but are not limited to, a xanthene dye, e.g. fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G ($R6G^5$ or $G^5$), 6-carboxyrhodamine-6G ($R6G^6$ or $G^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy2, Cy3, Cy3.5, Cy5, Cy5.5, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), 6-carboxy-2',4',7',4,7-hexachlorofluorescein (HEX), 6-carboxy-4',5'-dichloro-2',7'-dimethoxyfluorescein (JOE or J), Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, 7-amino-4-methylcoumarin-3-acetic acid, BODIPY FL, BODIPY FL-Br.sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, conjugates thereof, and combinations thereof. Exemplary lanthanide chelates include europium chelates, terbium chelates and samarium chelates. In some instances, the fluorophore is fluorescein.

In some embodiments of the method, the peroxidase substrate includes a fluorescent compound that includes 4 ferulic acid groups and a fluorescein connected via a linker (e.g., as described herein). In certain embodiments, the fluorescent compound is Fer-4-Flu:

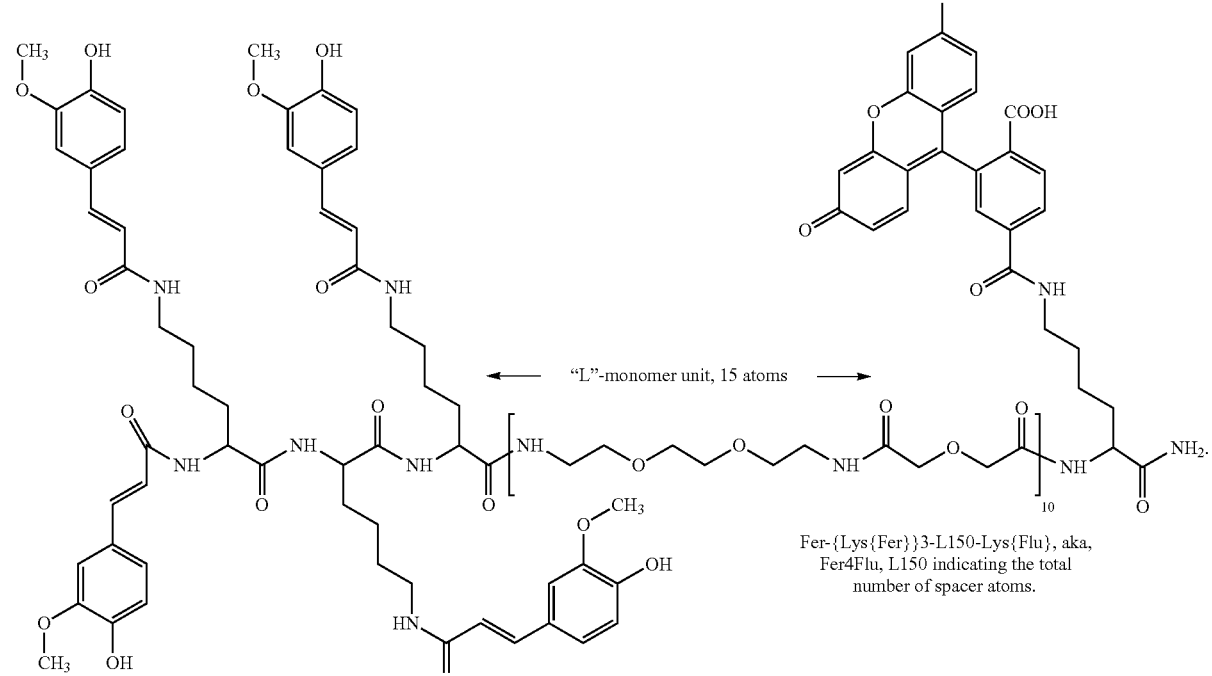

Fer-{Lys{Fer}}3-L150-Lys{Flu}, aka, Fer4Flu, L150 indicating the total number of spacer atoms.

Fer-4-Flu

The peroxidase substrate may include a mixture of two or more compounds, optionally comprised in a solvent, where each of the two or more compound is a substrate for the peroxidase. In some embodiments, the peroxidase includes a crosslinker that is capable of being acted upon by a peroxidase enzyme of interest to produce a phenoxyl radical initiator of radical chain polymerization (e.g., as described herein). The immobilized peroxidase may act upon the crosslinker to produce an insoluble adduct that precipitates in the vicinity of the peroxidase. In some cases, the insoluble adduct is a chromophore. In general terms, a crosslinker may be utilized as a peroxidase substrate in conjunction with the fluorescent compound to control the diffusion of the fluorescent compound (e.g., as described above) and maintain the fluorescent compound in close proximity to the immobilized peroxidase. In some cases, following activation by the peroxidase, the crosslinker reacts via radical chain polymeration with a further peroxidase substrate including a phenol-containing group (e.g., ferulic or cinnamic acid) to form a covalently linked product. Any convenient small molecules that are capable of reaction with a peroxidase activated phenol-containing group (e.g., as described herein) may be utilized to polymerize or crosslink to a peroxidase substrate.

As such, in some embodiments of the method the immobilized peroxidase may act upon two or more compounds, e.g., a fluorescent compound and a crosslinker. Any convenient crosslinkers may be utilized in the subject methods. Crosslinkers of interest include, but are not limited to, crosslinkers that find use in catalyzed reporter deposition (CARD) methods, 3,3'-diamino benzidin (DAB) and alpha-cyano-4-hydroxy-cinnamic acid (α-CHC).

In some embodiments of the method, the peroxidase substrate includes a fluorescent compound and a crosslinker capable of peroxidase-catalyzed radical chain polymerization to produce an insoluble adduct. In certain embodiments, the crosslinker is selected from 3,3'-diamino benzidin (DAB) and alpha-cyano-4-hydroxy-cinnamic acid (α-CHC). In certain instances, the crosslinker is 3,3'-diamino benzidin (DAB). In some instances, the crosslinker is alpha-cyano-4-hydroxy-cinnamic acid (α-CHC).

Many of the methods steps, reagents, enzymes and chemicals used in this step of the method may be adapted from a variety of publications, including, e.g., Lohse et al (Bioconjug Chem. 2014 25:1036-42), EP2398907, EP2398908, U.S. Pat. No. 8,435,735, WO2009036760 and WO2012143010, which are incorporated by reference herein.

After the peroxidase reaction, the labeled cells can be examined using a variety of different techniques, e.g., by microscopy, such as light microscopy, fluorescent microscopy or confocal microscopy. In embodiments in which oligonucleotides are labeled with a fluorescent moiety, reading of the sample to detect hybridization of labeled oligonucleotides may be carried out by fluorescence microscopy. Fluorescent microscopy, including confocal microscopy and structured illumination microscopy (SIM), has an added advantage of distinguishing multiple labels even when the labels overlap spatially. Methods of reading fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361. In certain embodiments, the microscope may be a high resolution microscope such as that described in Bates et al (Science 2007 317: 1749-1753).

Development of other enzyme/substrate pairs should also be considered to enable multicolor FISH. Alternatively, if multiple enzymes are not possible, HRP activity can be quenched vis hydrogen peroxide and multiplexing can be done sequentially. For example, FISH probes labeled with FITC, Texas Red, and Biotin could be used and sequentially amplified with anti-FITC-HRP, anti-TexasRed-HRP, and streptavidin-HRP. Each sequential reaction would then turn over a different color substrate (ie FITC, Cy3, and Cy5). In these embodiments, any a distinguishable pairs of dyes may be used such as Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable fluorophores may be found in Kricka et al. (Ann Clin Biochem. 39:114-29, 2002).

The method described above is compatible with both DNA and RNA FISH, as well as several commercial methods such as IQ FISH and SureFISH. The method can be performed on, e.g., FFPE sections and cell cultures, and is sufficiently sensitive to enable RNA-FISH using double stranded probes In certain embodiments, the signals obtained from performing the method may be compared with that of a reference sample, e.g., a cell from a healthy or wild-type sample. Briefly, the method comprises contacting under in situ hybridization conditions a test sample with a plurality of probes described above and contacting under in situ hybridization conditions a reference chromosome with the same plurality probes. After hybridization, the signals created from the unique binding patterns from the test sample are compared against those of the reference sample.

In some embodiments, a binding pattern obtained from a test sample may be compared to the pattern of binding of the same probes with a reference sample. The binding pattern of the reference sample may be determined before, after or at the same time as the binding pattern for the test sample. This determination may be carried out either manually or in an automated system. In certain cases, the signal associated with the test sample can be compared to the binding pattern that would be expected for known deletions, insertions, translocation, fragile sites and other more complex rearrangements, and/or refined breakpoints. The matching may be performed by using computer-based analysis software known in the art. Determination of identity may be done manually (e.g., by viewing the data and comparing the signatures by hand), automatically (e.g., by employing data analysis software configured specifically to match optically detectable signature), or a combination thereof.

In certain instances, the sample analyzed may be a tissue biopsy obtained from a patient. Biopsies of interest include both tumor and non-neoplastic biopsies of skin (melanomas, carcinomas, etc.), soft tissue, bone, breast, colon, liver, kidney, adrenal gland, gastrointestinal tissue, pancreas, gall bladder, salivary gland, cervical, ovary, uterus, testis, prostate, lung, thymus, thyroid, parathyroid, pituitary (adenomas, etc.), brain, spinal cord, ocular tissue, nerve, and skeletal muscle, etc.

The above-described method can be used to analyze cells from a subject to determine, for example, whether the cell is normal or not or to determine whether the cells are responding to a treatment. In one embodiment, the method may be employed to determine the degree of dysplasia in cancer cells. In these embodiments, the cells may be a sample from a multicellular organism. A biological sample may be isolated from an individual, e.g., from a soft tissue. In particular cases, the method may be used to distinguish different types of cancer cells in FFPE samples.

In some embodiments, the method may include forwarding data in electronic form to a remote location, where it can be analyzed by a doctor or other medical professional to determine whether a patient has abnormal cells (e.g., cancerous cells) or which type of abnormal cells are present. The data may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

In any embodiment, data can be forwarded to a "remote location," where "remote location" means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but be separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or include email transmissions and information recorded on websites and the like. In certain embodiments, the image may be analyzed by an MD or other qualified medical professional, and a report based on the results of the analysis of the image may be forwarded to the patient from which the sample was obtained.

EXEMPLARY EMBODIMENTS

A method of detecting a target nucleic acid is provided. In any embodiment, this method may comprise: obtaining a labeled nucleic acid probe that is complementary to a target nucleic acid, wherein the probe comprises a capture tag; hybridizing the probe with the target nucleic in a fixed cell, in situ, to produce a duplex; linking the probe in the duplex to a peroxidase conjugate via the capture tag to produce a peroxidase-labeled duplex; and incubating the peroxidase-labeled duplex with a peroxidase substrate, wherein the peroxidase activity of the peroxidase conjugate catalyzes deposition of the substrate in the vicinity of the duplex, thereby producing a detectable signal.

In any embodiment, the capture tag may be an affinity tag and wherein step (c) comprises non-covalently binding the peroxidase conjugate to the duplex.

In any embodiment, the capture tag may comprise a chemoselective functional group and step (c) comprises covalently linking the peroxidase conjugate to the duplex.

In any embodiment, the peroxidase substrate may comprise a fluorescent compound described by the formula:

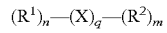

wherein each $R^1$ is independently, a phenol-containing group, a ferulic acid, a cinnamic acid or a cinnapinic acid group;

each $R^2$ is a fluorophore;

each X is a linker group or a chemical bond; and m, n and q are each independently an integer from 1 to 10.

In any embodiment, the fluorescent compound may be Fer-4-Flu.

In any embodiment, the peroxidase substrate may comprise a fluorescent compound and a crosslinker capable of peroxidase-catalyzed radical chain polymerization to produce an insoluble adduct.

In any embodiment, the crosslinker may be selected from 3,3'-diamino benzidin (DAB) and alpha-cyano-4-hydroxycinnamic acid (α-CHC).

In any embodiment, the labeled nucleic acid probe may comprise a PNA, a RNA or a DNA sequence complementary to the target nucleic acid.

In any embodiment, the labeled nucleic acid probe may be at least 20 nucleotides in length.

In any embodiment, the labeled nucleic acid probe may be single-stranded.

In any embodiment, the labeled nucleic acid probe may be double-stranded and the capture tag is present in only one strand of the probe.

In any embodiment, the labeled nucleic acid probe may be double-stranded and the capture tag is present in both strands of the probe.

In any embodiment, the cell may be in a tissue section.

In any embodiment, the cell may be in a formalin-fixed, paraffin-embedded (FFPE) tissue section.

In any embodiment, the capture tag may be selected from a hapten and a biotin moiety.

In any embodiment, the capture tag may comprise a chemoselective group selected from the group consisting of an alkyne, a cyclooctyne, an azide, a phosphine, a maleimide, a thiol, an alkoxyamine and an aldehyde.

In any embodiment, the capture tag may be a fluorescein and the peroxidase conjugate comprises an anti-fluorescein antibody.

In any embodiment, the capture tag may be biotin and the peroxidase conjugate comprises a streptavidin.

In any embodiment, the peroxidase conjugate may comprise an HRP polymer.

In any embodiment, the peroxidase conjugate may be an HRP-azide conjugate or an HRP-cyclooctyne conjugate.

In any embodiment, the peroxidase enzyme may be horse radish peroxidase (HRP) or soybean peroxidase (SP).

EXAMPLES

Aspects of the present teachings can be further understood in light of the following examples, which should not be construed as limiting the scope of the present teachings in any way.

The signal amplification method described herein works by using HRP to turn over a fluorescent substrate, e.g., Fer-4-Flu. In addition, a crosslinker (αCHC) is used to control the diffusion of the substrate and to maintain it in close proximity to the original probe location. Fer-4-Flu compound is shown in FIG. 1. This amplification requires FISH probes to be labeled with HRP. In the current embodiment, FISH probes are labeled with FITC during PCR amplification of the OLS libraries, either via labeled primers, labeled nucleotides, or both. ULS labeling with a FITC derived fluorophore is an alternative approach. An anti-FITC-HRP conjugate is then used to label the FISH probes with HRP. One implementation of this method is described below.

Reagents:

FITC-labeled oligonucleotide probes, reagents for in situ hybridization, wash buffer, H0236 Buffer (diluent buffer for antiFITC-HRP), anti-FITC HRP, substrate buffer, αCHC (crosslinker), Fer4-L150-Flu (substrate) and peroxidase blocking solution.

Current Procedure:
1. Perform standard FISH protocol with FISH probes labeled with FITC (either SureFISH or IQ FISH). Stop after last wash step. Do not dehydrate.
2. Block (5-10 min) Room temp DAKO peroxidase block
3. Wash (2×3 min) in DAKO Wash buffer
4. Anti-FITC-HRP (10-30 min) Room temp incubation with 10-20 nM antiFITC-HRP in H0236 buffer
5. Wash (2×3 min) in DAKO Wash buffer
6. Precipitation step (5 min) Room temp incubation with 1-10 μM Fer4Flu, 1-5 mg/mL αCHC, and 0.002% hydrogen peroxide in substrate buffer
7. Wash (2×3 min) in DAKO Wash buffer followed by (1×3 min) in water Dehydrate and Mount (standard protocol)

Results:

DNA FISH experiments showed the signal amplification system can amplify an FITC signal in oligonucleotide FISH experiments, for both FFPE and slide grown cells using IQ hybridization conditions or SureFISH hybridization conditions. Amplification was also shown for bacteria FISH in FFPE. All signals were amplified to a level strong enough to be visualized through the eye pieces of a microscope at 63× without additional aid from a camera. Representative images are shown in FIGS. 2-5.

Results also show that signal amplification system also works for RNA FISH, both with single and double stranded libraries, and for a variety of transcripts ranging from 23 kb down to 1.25 kb (data not shown).

It will also be recognized by those skilled in the art that, while the invention has been described above in terms of certain embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

What is claimed is:

1. A method of detecting a target nucleic acid, the method comprising:
    (a) obtaining a labeled nucleic acid probe for a target nucleic acid, wherein the probe is double-stranded and comprises a capture tag in only one strand of the probe, and wherein the one strand comprising the capture tag is complementary to the target nucleic acid;
    (b) contacting both strands of the probe, in denatured form, with the target nucleic acid under conditions suitable for nucleic acid hybridization, to produce a duplex comprising the capture tag and a target nucleic acid;
    (c) linking the probe in the duplex to a signal amplification conjugate via the capture tag; and
    (d) producing an amplified detectable signal from the signal amplification conjugate in the duplex.

2. The method of claim 1, wherein the capture tag is an affinity tag.

3. The method of claim 2, wherein the affinity tag is selected from a hapten and a biotin moiety.

4. The method of claim 1, wherein the capture tag comprises a chemoselective functional group.

5. The method of claim 4, wherein the chemoselective functional group is selected from the group consisting of an alkyne, a cyclooctyne, an azide, a phosphine, a maleimide, a thiol, an alkoxyamine and an aldehyde.

6. The method of claim 1, wherein the labeled nucleic acid probe comprises a PNA, a RNA or a DNA sequence complementary to the target nucleic acid.

7. The method of claim 1, wherein the labeled nucleic acid probe is at least 20 nucleotides in length.

8. The method of claim 1, wherein the target nucleic acid is in a cell.

9. The method of claim 8, wherein the cell is in a tissue section.

10. The method of claim 8, wherein the cell is in a formalin-fixed, paraffin-embedded (FFPE) tissue section.

11. The method of claim 1, wherein:
    linking step (c) comprises linking the probe in the duplex to an enzyme conjugate via the capture tag to produce an enzyme-labeled duplex; and
    producing step (d) comprises incubating the enzyme-labeled duplex with an enzyme substrate, wherein the enzymatic activity of the enzyme conjugate produces the amplified detectable signal.

12. The method of claim 11, wherein the enzyme substrate comprises a fluorescent compound described by the formula:

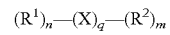

wherein each $R^1$ is independently, a phenol-containing group, a ferulic acid, a cinnamic acid or a cinnapinic acid group;
each $R^2$ is a fluorophore;
each X is a linker group or a chemical bond; and
m, n and q are each independently an integer from 1 to 10.

13. The method of claim 12, wherein the fluorescent compound is Fer-4-Flu.

14. The method of claim 11, wherein the enzyme substrate comprises a fluorescent compound and a crosslinker capable of peroxidase-catalyzed radical chain polymerization to produce an insoluble adduct.

15. The method of claim 14, wherein the crosslinker is selected from 3,3'-diamino benzidin (DAB) and alpha-cyano-4-hydroxy-cinnamic acid (α-CHC).

16. The method of claim 11, wherein the enzyme conjugate is a peroxidase conjugate and the enzyme substrate is a peroxidase substrate.

17. The method of claim 16, wherein the peroxidase conjugate comprises an HRP polymer.

18. The method of claim 17, wherein the peroxidase conjugate is an HRP-azide conjugate or an HRP-cyclooctyne conjugate.

19. The method of claim 17, wherein the peroxidase enzyme is horse radish peroxidase (HRP) or soybean peroxidase (SP).

20. The method of claim 1, wherein the target nucleic acid is an RNA transcript.

* * * * *

UNITED STATES PATENT AND TRADEMARK OFFICE
CERTIFICATE OF CORRECTION

PATENT NO. : 9,890,417 B2
APPLICATION NO. : 14/531563
DATED : February 13, 2018
INVENTOR(S) : Kristin Bernick et al.

It is certified that error appears in the above-identified patent and that said Letters Patent is hereby corrected as shown below:

On the Title Page

In item (56), in Column 2, under "Other Publications", Line 8, delete "Researcil," and insert -- Research, --, therefor.

In the Specification

In Column 4, Line 2, delete "formaldehye," and insert -- formaldehyde, --, therefor.

In Column 12, Line 11, delete "Napthofluorescein," and insert -- Naphthofluorescein, --, therefor.

In Column 12, Line 12, delete "Napthofluorescein," and insert -- Naphthofluorescein, --, therefor.

In Column 13, Line 18, delete "polymeration" and insert -- polymerization --, therefor.

In Column 14, Line 28, after "probes" insert -- . --.

Signed and Sealed this
Ninth Day of October, 2018

Andrei Iancu
*Director of the United States Patent and Trademark Office*